United States Patent [19]
Aki et al.

[11] Patent Number: 4,976,705
[45] Date of Patent: Dec. 11, 1990

[54] MOLDED GERMANIUM AND CERAMIC ARTICLE FOR SKIN CONTACT MEDICAL TREATMENT

[75] Inventors: Osami Aki, Kawanishi; Yoshinori Yamamoto, Urayasu; Masayoshi Matsuoka, Habikino; Nakao Mikami, Kusatsu, all of Japan

[73] Assignees: Kyocera Corporation, Kyoto; Takeda Chemical Industries, Ltd., Osaka, both of Japan

[21] Appl. No.: 366,134

[22] Filed: Jun. 14, 1989

[30] Foreign Application Priority Data

Jun. 20, 1988 [JP] Japan ................................. 63-153306

[51] Int. Cl.$^5$ ............................................. A61F 13/00
[52] U.S. Cl. ...................................... 604/304; 604/20; 128/399
[58] Field of Search ................... 604/20, 23, 289, 290, 604/291, 307, 304; 128/399, 401; 357/28, 81

[56] References Cited

U.S. PATENT DOCUMENTS 4,657,531 4/1987 Choi ..................................... 604/23
4,781,705 11/1988 Shepherd et al. ................... 604/304

OTHER PUBLICATIONS

Derwent Accession No. 87—309163.
Derwent Accession No. 87—303614.
Derwent Accession No. 88—087891.
Derwent Accession No. 87—133273.
Derwent Accession No. 86—295163.

Primary Examiner—Alan Cannon
Attorney, Agent, or Firm—Wenderoth, Lind & Ponack

[57] ABSTRACT

A molded article for skin contact medical treatment which comprises an integrally molded product of germanium and ceramic which irradiates far infrared rays by heating.

6 Claims, 1 Drawing Sheet

MOLDED GERMANIUM AND CERAMIC ARTICLE FOR SKIN CONTACT MEDICAL TREATMENT

FIELD OF THE INVENTION

The present invention relates to a molded article for skin contact medical treatment. More particularly, it relates to a device for medical treatment which is a molded article of germanium and a far infrared ray irradiating ceramic and is used by bringing it into contact with the skin such as a diseased part of the human body, an effective spot of the skin and the like.

BACKGROUND OF THE INVENTION

As can be seen from the fact that well known herb medicines such as ginseng, a bracket fungus of the genus Fomes and, the like contain organic germanium, recently, the use of germanium has been noted in medical treatment.

Usually, organic germanium is administered orally. On the other hand, inorganic germanium is locally applied to the skin in the form of a magnetic material for medical treatment by bringing it into contact with an affected spot of the skin and the like. For example, Japanese Patent Laid Open Publication No. 117187/1979 discloses germanium which is a metal piece in the form of a substantially circular small disk and is brought into contact with the skin by pressing it against the skin with a plaster or the like.

Although these germanium materials manifest analgetic and antiphlogistic effects such as therapeutic effect on stiff shoulders, lumbago and muscular ache, its mechanism has not yet been clarified.

However, there is an opinion that, when germanium is applied to a diseased part, it removes an abnormal electric potential of the human body by electron interchange to bring the body back to the normal electric potential because:

(1) germanium is apt to be positively charged due to escape out of the peripheral electron (i.e., germanium has a strong electrophilic properties); and (2) a diseased part or a body part with stiffness or pain generally has an increased elect-ron potential.

Further, it is presumed that the above metal piece of germanium stimulates an affected spot of the skin by pressing it against the skin with a plaster or the like to manifest certain therapeutic effect.

In any event, even if the above metal piece of germanium is applied to an affected spot of the skin with a plaster or the like, the contact surface is a mere flat surface. On the other hand, the affected spot of the skin is very small. Therefore, it is difficult to concentrate stimulation by pressing on the affected spot and there is a possibility that the therapeutical effect of germanium can not be strongly manifested.

Then, Japanese Utility Model Laid Open Publication No. 133339/1983 discloses an improved device for medical treatment wherein germanium powder and activated charcoal powder are mixed and subjected to heat molding treatment such as sintering or the like to solidify the mixture into a molded article having fine uneven contact surface which can readily concentrate stimulation by pressing on an affected spot of the skin to improve its therapeutic effect. That is, this device is aimed at the improvement of the therapeutic effect of germanium by extending the active surface of germanium with utilizing electrical conductivity of activated charcoal in addition to concentration of stimulation. However, the fundamental effect on the human body is limited to the electrical activity of germanium alone and, therefore, its therapeutic effect is naturally limited.

On the other hand, some ceramics irradiate far infrared rays by absorption of heat energy when they are heated, and it has been known that, when the human body is exposed to such far infrared rays, they manifest various effects such as rise in deep subcutaneous temperature, angiotelectasia, enhancement of blood circulation and metabolism, mitigation of sensory nerves, regulation of autonomic nerves and the like.

The present inventors have sought such a far infrared ray irradiating ceramic, and have found that, when germanium is mixed with the ceramic and the mixture is molded integrally, the therapeutic effect can be improved and the scope of treatment can be extended.

Japanese Patent Laid Open Publication No. 180979/1987 discloses a heating element of a warmer for warming the human body to enhance metabolism thereof which is a sintered molded article of a mixture of a far infrared ray irradiating ceramic, an oxide of a specific metal such as iron, manganese, chromium or the like, and metallic germanium or germanium oxide. However, this heating element is used by heating with a nichrome wire heater or the like and is different from a device for skin contact medical treatment. Further, in this heating element, at most, 10 parts by weight of germanium is used per 100 parts by weight of ceramic.

OBJECTS OF THE INVENTION

The main object of the present invention is to provide a molded article for skin contact medical treatment which can be readily and properly applied to an affected spot of the skin, and which is superior to the conventional medical treatment by germanium.

This object as well as other objects and advantages of the present invention will become apparent to those skilled in the art from the following description with reference to the accompanying drawings.

SUMMARY OF THE INVENTION

Figure 1:
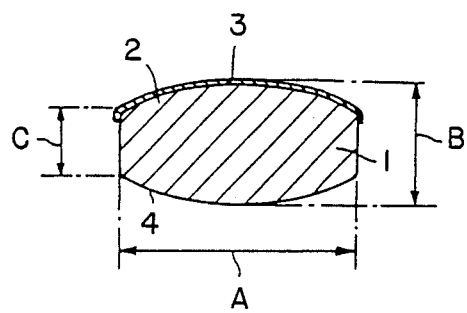
FIG. 1 is a schematic longitudinal cross section illustrating one embodiment of the article for skin contact medical treatment of the present invention.

According to the present invention, there is provided a molded article for skin contact medical treatment which comprises an integrally molded product of germanium and ceramic which irradiates far infrared rays by heating.

In the article of the present invention, the surface area of germanium which is effective to the human body is increased. Further, although the mechanism is unclear, it is considered that the therapeutic effect of germanium is enhanced by action of heat rays of far infrared rays irradiated from the ceramic by heating with the body temperature.

DETAILED DESCRIPTION OF THE INVENTION

Germanium to be used in the present invention may be any germanium or germanium containing substance including inorganic germanium, an organic germanium complex containing 2 to 10 carbon atoms and the like. In the case of inorganic germanium, preferably, it has a purity of not less than 99.9%.

The ceramic to be used in the present invention is not limited to a specific one insofar as it irradiates far infrared rays by heating with the body temperature. Examples thereof include far infrared ray irradiating ceramics obtained by sintering finely divided powder or previously calcined finely divided powder composed of $ZrO_2$, $MgO$, $Al_2O_3$, $SiO_2$, $Cr_2O_3$, $TiO_2$, $Fe_2O_3$ and the like alone or mixtures thereof, or by pulverizing these substances without sintering. Preferably, the wavelength of far infrared rays irradiated is about 3 to 16μ, particularly, about 5 to 16μ because of its strong thermal resonance effect. However, insofar as thermal effect is obtained to a certain extent, the wavelength is not limited thereto.

Although the ratio of germanium and the ceramic is not specifically limited, generally, the molded article of the present invention contains germanium and the ceramic in the weight ratio of germanium (as inorganic pure germanium, hereinafter the amount of germanium is expressed according to the same manner unless otherwise stated): the ceramic of 10 to 90:90 to 10, preferably, 10 to 30:90 to 70.

Optionally, in addition to germanium and the ceramic, the molded article of the present invention can appropriately contain other materials, for example, blowing agents, bulk fillers, auxiliary fillers such as ceramics which do not irradiate far infrared rays and the like.

The molded article for skin contact medical treatment of the present invention is an integrally molded product of germanium and the ceramic. Examples of the integrally molded product include a molded product of a uniform powder mixture of germanium and the ceramic, a product obtained by integrally combining separately prepared molded material of the ceramic and that of germanium, and the like. For example, the molded article of the present invention can be prepared as follows:

(1) A powder mixture of germanium powder and sintered far infrared ray irradiating ceramic powder is filled in a mold having the desired shape (e.g., disk, ball, tube, etc.) and it is subjected to press molding. Optionally, the resulting molded article can be sintered.

(2) Powders of raw materials of the far infrared ray radiating ceramic are mixed and the resulting mixture is further admixed with germanium powder. The resulting powder mixture is press-molded and, if necessary, sintered.

(3) A sintered molded product in the shape of a cup, hollow tube, ball or the like is prepared from the far infrared ray irradiation ceramic powder, and germanium powder or germanium powder containing a binder and the like is filled in the cup or tube. If necessary, the cup or tube is sealed with a metallic film as described hereinafter. Or, the surface of the ball can be coated with germanium powder according to a known method.

(4) A molded product in the shape as described above is prepared from germanium powder or metallic germanium, and the ceramic is filled in the molded product or coated thereon.

(5) A disk of the ceramic is sandwiched with disks of germanium or vice versa.

In the present invention, when germanium is sintered, it is desirable to carry out sintering at a temperature at which germanium is not molten, e.g., 500° to 1000° C. Further, when germanium is oxidized, the therapeutic effect thereof is lowered. Therefore, the sintering is preferably carried out in a non-oxidative atmosphere, for example, in an atmosphere of inert gas such as nitrogen, argon or the like.

Optionally, the molded article of the present invention can further contain magnetized ferrite. Thereby, magnetic effect can be added and the therapeutic effect of the molded article is further improved. Ferrite can be uniformly admixed with germanium powder and ceramic powder. Alternatively, it can be used as the above molded product in the shape of a cup, tube, disk, ball or the like, or as a material to be filled therein. The amount of ferrite is preferably 1 to 20% by weight based on the molded article. In the production of the molded article containing ferrite, a magnetization step is required.

The molded article for skin contact medical treatment of the present invention can be used by applying it to the skin as it is with a plaster or the like. Further, preferably, one surface of the article of the present invention can be covered with a metallic film and the other surface thereof can be brought into contact with the skin. Thereby, electric and thermal effects can be concentrated on the skin.

For example, the metallic film can be formed by depositing a thin metal film on one surface of the article, or by adhering a metallic foil thereto. The metal is preferably aluminum from the viewpoint of economy and the like. However, there can be used tin, nickel and the like.

Further, according to the present invention, by using the plural molded articles, a necklace, bracelet or the like can be formed. By using such an article according to the same manner as a conventional necklace bracelet, medical treatment can be carried out in everyday life.

Upon applying the article to a diseased part of the body or an affected spot of the skin, the ceramic is warmed by the body temperature and far infrared rays are irradiated from the ceramic. At the same time, the electrical effect of germanium reaches the skin at the contact part. Thus, both therapeutic effects of germanium and ceramic can be manifested at the same time.

Further, electrophilic properties of germanium are enhanced because germanium absorbs a part of heat energy of far infrared rays irradiated from the ceramic to lose an electron, which increases the positive charged tendency of germanium. Therefore, it is expected that the therapeutic effect of the contact part of the skin is enhanced.

In addition, as described above, when one surface of the article is covered with a metallic film such as aluminum film and the other surface is brought into contact with the skin, diffusion of the electrical and thermal effects of the article toward directions other than the contact part can be prevented and the therapeutic effect can be concentrated on the skin area with which the article is brought into contact.

Thus, the following advantages can be obtained by the molded article for skin contact medical treatment of the present invention.

(1) Enhancement of analgetic and antiphlogistic effects of germanium is expected due to thermal effect of far infrared rays irradiated from the ceramic, since in comparison with the therapeutic effect of a conventional article for skin contact medical treatment containing germanium alone, heat ray the effect of the ceramic is added and effect of germanium itself is enhanced.

Therefore, the scope of treatment can be expanded and the therapeutic effect can be improved.

(2) In the molded article of the present invention, germanium and the ceramic are molded integrally and fine uneven contact surface is formed. Therefore, it is possible to concentrate stimulation by pressing on a diseased part or an affected spot.

(3) In the case of covering one surface of the molded article with a metallic film, the electrical and thermal effects can be concentrated on the body. Thereby, medical treatment can be carried out more effectively.

Hereinafter, the molded article for skin contact medical treatment of the present invention is further illustrated in detail with reference to the accompanying drawings.

FIG. 1 is a schematic longitudinal cross section illustrating one embodiment of the molded article for skin contact medical treatment of the present invention.

As shown in FIG. 1, the molded article 1 is molded in a substantially flat cylinder and both top and bottom surfaces thereof are somewhat curved convexly to provide a suitable stimulation by pressing softly.

The molded article 1 is 5 mm in diameter (A), 2.7 mm in thickness at the center part (B) and 1.5 mm in thickness at peripheral part (C) to provide a suitable contact surface area without leaving a depressed mark on the skin or causing pain.

The molded article 1 was prepared as follows.

Small amounts of sintering auxiliaries such as CaO, MgO and $Y_2O_3$ were added to $ZrO_2$ powder and the powder mixture was molded in the desired shape and sintered at 500° to 1000° C. to obtain a sintered mass. This was pulverized into finely divided powder having an average particle size of 0.1 to $5\mu$ to obtain sintered powder of the far infrared ray irradiating ceramic.

Germanium powder was prepared by pulverizing metallic germanium having high purity to obtain finely divided powder having an average particle size of 0.1 to $5\mu$.

The above finely divided germanium powder and finely divided ceramic powder were mixed in the a weight ratio of 10 (germanium): 90 (ceramic) uniformly with a ball mill. The powder mixture was filled in the desired mold and was press-molded and sintered by heating in a furnace or ambient calcination to solidify integrally.

Then, aluminum foil 3 was adhered to the top convex surface 2 and the bottom surface 4 was used for bringing into contact with the skin. Thereby, therapeutic effect was concentrated on the body 6 (see FIG. 2).

Figure 2:
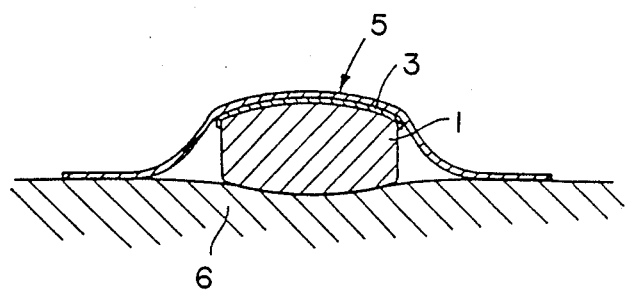
FIG. 2 is a schematic longitudinal cross section illustrating how to use the article of FIG. 1.

FIG. 2 is a schematic longitudinal cross section illustrating how to use the article of FIG. 1. The top surface of the molded article 1 on which the aluminum foil 3 was present was adhered to the center of a circular plaster 5 and the article 1 was applied to the skin 6 by pressing with the plaster so that the bottom surface 4 of the article 1 was applied to a diseased part or an affected spot of the skin.

The following clinical tests illustrate the therapeutic effect of the above article for skin contact medical treatment of the present invention.

TEST 1

The patient was a 52 year-old man suffering from serious pain and stiffness of the shoulders such that he could not raise his arms and hang on to a strap of a train. The above molded articles were applied to both shoulders as shown in FIG. 2. According to him, pain was mitigated within 3 days and he felt relieved.

TEST 2

The patient was a 35 year-old woman sometimes suffering from stiffness of the right shoulder with downhearted feeling. The above molded article was applied to the diseased part. According to her, stiffness was mitigated about 1 week.

TEST 3

The patient was a 54 year-old man suffering from stiffness of the shoulders, neck and back and he felt heavy in the eyes. The above molded article was applied to each diseased part. According to him, he felt relieved and stiffness of the neck was completely healed.

TEST 4

The patient was a 62 year-old man suffering from serious pain of the waist. He felt a pain when standing for a long period of time. When the above molded article was applied to the diseased part, the article relieved his pain of the waist on the next day. According to him, pain of the waist was gone after continuously applying the article for more than 1 month.

TEST 5

The patient was 50 year-old man. In his work, long term reading was required and, recently, he complained of fatigue of the eyes and shoulders. When the above molded articles were applied to both shoulders, fatigue of the shoulders was gone after 3 days. According to him, the article relieved his fatigue of the eyes and, by continuously applying the articles, conditions of the eyes and shoulders were much improved.

TEST 6

The patient was 53 year-old woman suffering from insomnia. When the above molded articles were applied to both ankles, she slept much better and deeper than usual and the sleeping time (6 hours) was longer than usual (4 hours).

What is claimed is:

1. A molded article for skin contact medical treatment which comprises an integrally molded product of germanium and ceramic which irradiates far infrared rays by heating.

2. A molded article according to claim 1, wherein a mixture of germanium powder and ceramic powder is molded, integrally.

3. A molded article according to claim 1, wherein the article contains germanium and ceramic in a weight ratio of germanium as inorganic pure germanium: ceramic of 10 to 90:90 to 10.

4. A molded article for skin contact medical treatment which comprises an integrally molded product of germanium and ceramic which irradiates far infrared rays by heating, wherein the molding is carried out by sintering in a non-oxidative atmosphere.

5. A molded article for skin contact medical treatment which comprises an integrally molded product of germanium and ceramic which irradiates far infrared rays by heating, wherein the molding is carried out without sintering.

6. A molded article for skin contact medical treatment which comprises an integrally molded product of germanium and ceramic which irradiates far infrared rays by heating, wherein one surface of the article which is not brought into contact with the skin is covered with a metallic film.

* * * * *